(12) United States Patent
Moriya

(10) Patent No.: US 8,338,630 B2
(45) Date of Patent: Dec. 25, 2012

(54) AMINO ACID GROUP-MODIFIED ORGANOPOLYSILOXANE AND SILANE, AMINO ACID GROUP-CONTAINING COMPOUND, AND PRODUCTION METHOD THEREOF

(75) Inventor: Hiroyuki Moriya, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 102 days.

(21) Appl. No.: 12/965,203

(22) Filed: Dec. 10, 2010

(65) Prior Publication Data

US 2011/0144369 A1   Jun. 16, 2011

(30) Foreign Application Priority Data

Dec. 11, 2009 (JP) ................... 2009-281099
Dec. 11, 2009 (JP) ................... 2009-281114
Dec. 11, 2009 (JP) ................... 2009-281126

(51) Int. Cl.
  *C07F 7/18* (2006.01)
(52) U.S. Cl. ........ 556/425; 556/433; 556/434; 556/466; 556/419; 424/59; 424/63; 424/78.03; 528/38
(58) Field of Classification Search .......... 556/419, 556/425, 433, 434, 416; 424/59, 63
See application file for complete search history.

(56) References Cited

U.S. PATENT DOCUMENTS

| 5,753,214 A | 5/1998 | Yoshioka et al. |
| 6,228,968 B1 | 5/2001 | Yoshioka et al. |
| 6,268,454 B1 * | 7/2001 | Song et al. ........ 528/12 |
| 6,358,501 B1 | 3/2002 | Dietz et al. |
| 2006/0269499 A1 * | 11/2006 | Gormley et al. ........ 424/70.12 |

FOREIGN PATENT DOCUMENTS

| JP | 63-301854 A | 12/1988 |
| JP | 3-223207 A | 10/1991 |
| JP | 8-59424 A | 3/1996 |
| JP | 11-140032 A | 5/1999 |
| JP | 2000-44554 A | 2/2000 |
| JP | 2000-143797 A | 5/2000 |
| JP | 2002-146011 A | 5/2002 |
| JP | 2003-160663 A | 6/2003 |
| JP | 2004-182680 A | 7/2004 |
| JP | 2004-269459 A | 9/2004 |
| WO | WO 2009/106486 A1 | 9/2009 |

OTHER PUBLICATIONS

European Search Report issued Jun. 14, 2011, in European Patent Application No. 10252085.5.

* cited by examiner

*Primary Examiner* — Johann Richter
*Assistant Examiner* — Pancham Bakshi
(74) *Attorney, Agent, or Firm* — Birch, Stewart, Kolasch & Birch, LLP

(57) ABSTRACT

An amino acid-modified organopolysiloxane is provided. It has an amino acid derivative bonded to at least one silicon atom of the organopolysiloxane segment constituting the backbone of the organopolysiloxane via an amide bond represented by the following general formula (1):

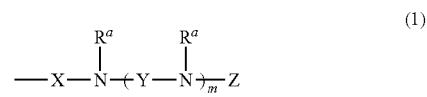

wherein X and Y are independently a $C_{1-10}$ divalent hydrocarbon group; m is an integer of 0 to 4; $R^a$ is hydrogen atom, a monovalent hydrocarbon group containing 1 to 4 carbon atoms, or an organic group represented by the following general formula (2):

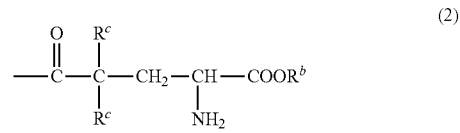

(wherein $R^b$ is hydrogen atom, a $C_{1-7}$ monovalent hydrocarbon group, an alkaline metal, or an alkaline earth metal, and $R^c$ is independently hydrogen atom, hydroxy group, or a $C_{1-10}$ monovalent hydrocarbon group optionally containing oxygen atom, sulfur atom, or nitrogen atom); and Z is an organic group represented by the general formula (2).

6 Claims, No Drawings

AMINO ACID GROUP-MODIFIED ORGANOPOLYSILOXANE AND SILANE, AMINO ACID GROUP-CONTAINING COMPOUND, AND PRODUCTION METHOD THEREOF

CROSS-REFERENCE TO RELATED APPLICATION

This non-provisional application claims priority under 35 U.S.C. §119(a) on Patent Application Nos. 2009-281099, 2009-281114 and 2009-281126 filed in Japan on Dec. 11, 2009, Dec. 11, 2009 and Dec. 11, 2009, respectively, the entire contents of which are hereby incorporated by reference.

TECHNICAL FIELD

This invention relates to an amino acid-modified organopolysiloxane and silane, an amino acid group-containing compound, and production method thereof.

BACKGROUND ART

Various compounds and methods have been investigated for use in producing an amino acid-modified or a peptide-modified silicone and for use in its production method.

For example, in the case of a silicone modified with an amino acid derivative represented by the following formula:

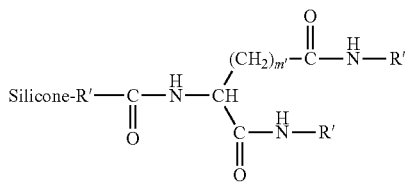

the silicone has a structure in which the amino group and the carboxy group of the amino acid have been protected. In addition, this silicone has been produced by using various toxic compounds such as isocyanate and dicyclohexyl carbodiimide, and this is unfavorable in view of safety. Furthermore, the compound having such complicated structure can not be produced by a simple procedure (JP-A 2004-182680).

A silicone modified with an amino acid derivative represented by the following formula:

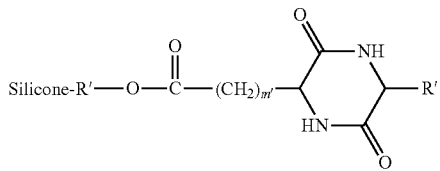

also suffers from the problem that it is produced by using a protected amino acid derivative whose synthesis not easy (JP-A 2004-269459).

A peptide-silicone copolymer represented by the following formula:

has been produced by a method using generation of polysuccinimide from aspartic acid. However, this method is dangerous since a temperature as high as at least 160° C. is required. In addition, unnecessary components are generated by side reaction, and this leads to the need of filtration and washing as well as low yield (JP-A 2000-143797).

JP-A H3-223207 discloses a method in which a silicone having one epoxy-modified end is reacted with the amino group of a peptide. However, this method is unfavorable since the epoxy-modified silicone used as the reactant is toxic.

JP-A H11-286550 discloses hydrolytic copolymerization of a peptide-containing silane with an alkoxysilane or the like. This method, however, suffered from the problem of insufficient storage stability since the amino group and the carboxyl group from the peptide-containing silane formed —Si—NH— and —Si—OOC— which are less resistant to hydrolysis.

For the organosilane compounds, JP-A H8-59424 discloses a polypeptide-containing silane as a compound having both the amino group and the carboxyl group introduced in one molecule. For the amino acid-modified silane compound, JP-A 2002-146011 and JP-A 2003-160663 disclose an amino acid group-containing silane produced by reacting an amino functional silane and an α-amino acid-N-carboxylic acid anhydride. The compound disclosed in the JP-A H8-59424 is a compound having a polypeptide bonded to the silane and not a compound constituted by the monomeric amino acid units linked together. This compound also has the problem of toxicity due to its use of epoxy-modified silane. The amino acid group-containing silane disclosed in the JP-A 2002-146011 and JP-A 2003-160663 is the one produced from an α-amino acid-N-carboxylic acid anhydride and an amino-modified silane, and the α-amino acid-N-carboxylic acid anhydride is very expensive, and has the problem that it is not readily available in the commercial market.

In view of such situation, a novel amino acid-modified silane which can be produced from highly safe starting materials in a convenient manner at a high yield is highly awaited. In addition, an amino acid-modified silane synthesized from an amino-modified silane and a pyroglutamine acid derivative is still unknown in the art.

Furthermore, JP-A H11-140032 discloses production of a N-long chain acyl acidic amino acid by reaching an acidic amino acid with a fatty acid halide as a derivative having a long chain alkyl group or a fatty acid bonded to the amino acid. JP-A S63-301854 discloses production of a neutral amino acid —N-carboxylic acid anhydride by using phosgene. JP-A 2000-44554 discloses a production method of an amino acid anhydride as well as a production method of its derivatives. In the case of the amino acid group-containing compound disclosed in the JP-A H11-140032, the hydrophilic group in the resulting product would only be the carboxyl group since the amino group is reacted with the acid chloride. The compound also suffers from the problem of the chlorine compound generated from the fatty acid chloride remaining in the resulting product. The amino acid group-containing compounds disclosed in JP-A S63-301854 and

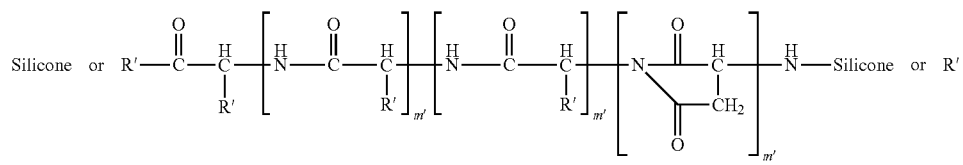

JP-A 2000-44554 are unsafe due to the use of phosgene in their production, and the production cost is also high.

By the way, the method of bonding an aliphatic amine, a higher aliphatic amine, or a hydroxy aliphatic amine with an pyroglutamine acid derivative through amide bond, and the an amino acid group-containing compound having both the amino group and the carboxyl group as the hydrophilic groups produced by such method are unknown in the art.

In view of such situation, a strong need exists for the development of a novel amino acid group-containing compound which has a hydrocarbon group as the lipophilic group and carboxyl group and amino group as the hydrophilic group, and which can be produced from highly safe starting materials in a convenient manner at a high yield.

SUMMARY OF INVENTION

Accordingly, an object of the present invention is to provide a novel amino acid-modified organopolysiloxane, and a method for producing such a novel amino acid-modified organopolysiloxane from highly safe starting materials in a convenient manner at a high yield.

Another object of the present invention is to provide a novel amino acid-modified silane, and a method for producing such a novel amino acid-modified silane from highly safe starting materials in a convenient manner at a high yield.

A still another object of the present invention is to provide a novel amino acid group-containing compound, and a method for producing such a novel amino acid group-containing compound from highly safe starting materials in a convenient manner at a high yield.

In order to realize the objects as described above, the inventors of the present invention made an intensive study, and found that a novel amino acid-modified organopolysiloxane can be produced in a convenient manner and at a high yield from an amino-modified organopolysiloxane and a pyroglutamine acid derivative which are highly safe starting materials.

Accordingly, the first aspect of the present invention is an amino acid-modified organopolysiloxane and a method for producing such an amino acid-modified organopolysiloxane.

[1] An amino acid-modified organopolysiloxane having an amino acid derivative bonded to at least one silicon atom of the organopolysiloxane segment constituting the backbone of the amino acid-modified organopolysiloxane via an amide bond represented by the following general formula (1):

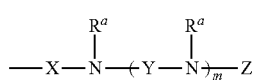

wherein
X and Y are independently a divalent hydrocarbon group containing 1 to 10 carbon atoms;
m is an integer of 0 to 4;

$R^a$ is a group selected from hydrogen atom, a monovalent hydrocarbon group containing 1 to 4 carbon atoms, and an organic group represented by the following general formula (2):

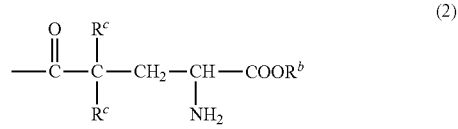

(wherein $R^b$ is hydrogen atom, a monovalent hydrocarbon group containing 1 to 7 carbon atoms, an alkaline metal, or an alkaline earth metal, and $R^c$ is independently hydrogen atom, hydroxy group, or a monovalent hydrocarbon group containing 1 to 10 carbon atoms optionally containing oxygen atom, sulfur atom, or nitrogen atom); and Z is an organic group represented by the general formula (2).

[2] An amino acid-modified organopolysiloxane according to the above [1] which is a compound represented by the average compositional formula (3):

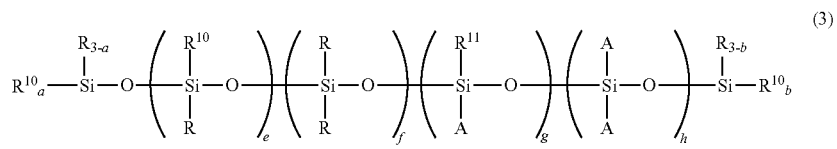

wherein
R is independently a group selected from hydrogen atom, hydroxy group, an alkyl group containing 1 to 30 carbon atoms, a fluoroalkyl group containing 1 to 30 carbon atoms, an aryl group containing 6 to 30 carbon atoms, and an aralkyl group containing 7 to 30 carbon atoms,
$R^{10}$ is an organic group represented by the general formula (1) of the above [1],
$R^{11}$ is an organic group selected from $R^{10}$ and R,
A is an organopolysiloxane segment represented by the following general formula (4):

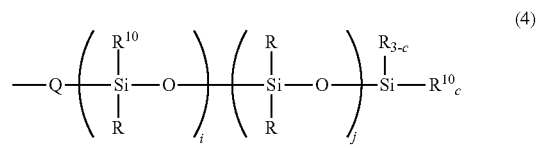

(wherein R and $R^{10}$ are as defined above, and Q is oxygen atom or a divalent hydrocarbon group containing 1 to 3 carbon atoms), and in the formula (3) and general formula (4),
a, b, and c are independently an integer of 0 to 3,
e is an integer of 0 to 500,
f is an integer of 0 to 50,000,
g is an integer of 0 or 1,
h is an integer of 0 or 1,
i is an integer of 0 to 500, j is an integer of 0 to 10,000, with the proviso that, $1 \leq a+b+c+e+g+i$ when $R^{11}$ is the same as $R^{10}$ and $1 \leq a+b+c+e+i$ when $R^{11}$ is the same as R.

[3] A method for producing the amino acid-modified organopolysiloxane of the above [1] or [2] comprising the step of reacting an amino-modified organopolysiloxane having an amino group bonded to at least one silicon in the organopolysiloxane segment constituting the backbone of the amino-modified organopolysiloxane wherein the amino group is represented by the following general formula (5):

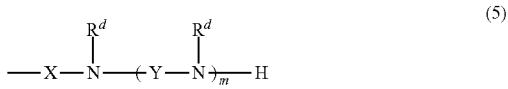

wherein X, Y, and m are as defined in the above [1], and $R^d$ is hydrogen atom or a monovalent hydrocarbon group containing 1 to 4 carbon atoms with a compound represented by the following general formula (6):

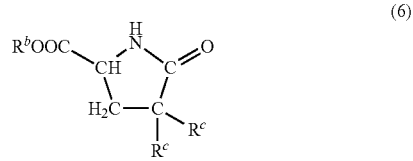

wherein $R^b$ and $R^c$ are as defined in the above [1].

[4] A method for producing an amino acid-modified organopolysiloxane according to the above [3] wherein the amino-modified organopolysiloxane is the one represented by the following average compositional formula (7):

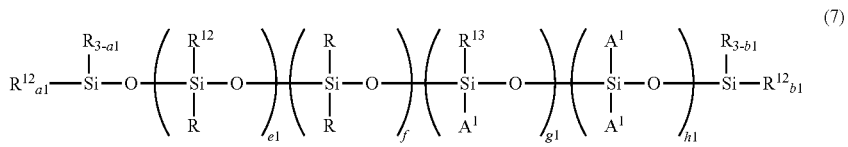

wherein R is as defined in the above [2], $R^{12}$ is an organic group represented by general formula (5) of the above [3], $R^{13}$ is an organic group selected from $R^{12}$ and R, and $A^1$ is an organopolysiloxane segment represented by the following general formula (8):

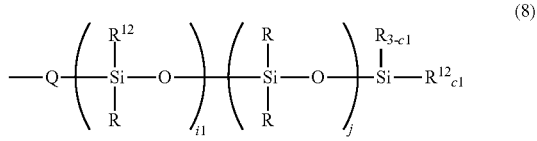

(wherein R and $R^{12}$ are as defined above), and
wherein, in the formula (7) and the general formula (8),
a1, b1, and c1 are independently an integer of 0 to 3,
e1 is an integer of 0 to 500,
f is an integer of 0 to 50,000, and
g1 is an integer of 0 of 1,
h1 is an integer of 0 or 1,
i1 is an integer of 0 to 500, and
j is an integer of 0 to 10,000,
with the proviso that $1 \leq a1+b1+c1+e1+g1+i1$ when $R^{13}$ is $R^{12}$ and $1 \leq a1+b1+c1+e1+i1$ when $R^{13}$ is R.

[5] A method according to the above [3] or [4] wherein the reaction is conducted under temperature conditions of 50 to 160° C.

[6] A method according to any one of the above [3] to [5] wherein the compound represented by the general formula (6) is pyroglutamine acid.

This amino acid-modified organopolysiloxane has carboxyl group and amino group which are hydrophilic groups, and therefore, it is well adapted for use in the applications such as cosmetics, powder surface treatment, fiber treatment, coating composition, and resin modification. The production method of the present invention is capable of producing the amino acid-modified organopolysiloxane from highly safe starting materials in a convenient manner with no byproducts and at a high yield with no need for further purification.

The inventors of the present invention also found that an amino acid-modified silane can be produced by reacting an amino group-containing silane compound with a pyroglutamine acid derivative with no byproducts and at a high yield.

Accordingly, the second aspect of the present invention is an amino acid-modified silane and a method for producing the amino acid-modified silane.

[7] An amino acid-modified silane represented by the following general formula (9):

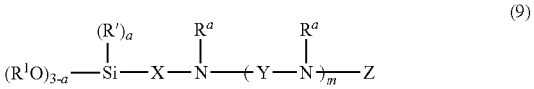

wherein
X and Y are independently a divalent hydrocarbon group containing 1 to 10 carbon atoms, R' is independently a group selected from hydrogen atom, a monovalent alkyl group containing 1 to 30 carbon atoms, a monovalent fluoroalkyl group containing 1 to 30 carbon atoms, a monovalent aryl group containing 6 to 30 carbon atoms, and a monovalent aralkyl group containing 7 to 30 carbon group, $R^1$ is independently hydrogen atom or a monovalent hydrocarbon group containing 1 to 10 carbon atoms, $R^a$ is a group selected from hydrogen atom, a monovalent hydrocarbon group containing 1 to 4 carbon atoms, and a group represented by the following general formula (2):

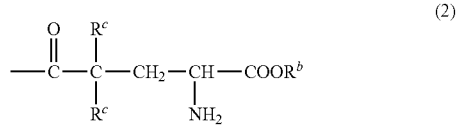

(wherein $R^b$ is hydrogen atom, a monovalent hydrocarbon group containing 1 to 7 carbon atoms, an alkaline metal, or an alkaline earth metal, $R^c$ is independently hydrogen atom, hydroxy group, or a monovalent hydrocarbon group containing 1 to 10 carbon atoms optionally containing oxygen atom, sulfur atom, or nitrogen atom), a is an integer of 0 to 3, m is an integer of 0 to 4, and Z is an organic group represented by the general formula (2).

[8] A method for producing the amino acid-modified organopolysiloxane of the above [7] comprising the step of reacting an amino-modified silane having an amino group bonded thereto wherein the amino group is represented by the following general formula (10):

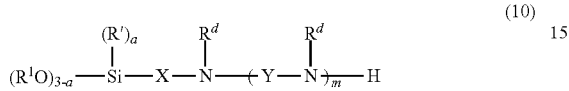
(10)

wherein R', $R^1$, X, Y, and m are as defined in the above [7], and $R^d$ is hydrogen atom or a monovalent hydrocarbon group containing 1 to 4 carbon atoms with a compound represented by the general formula (6):

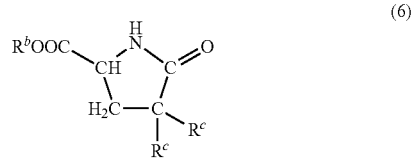
(6)

wherein $R^b$ and $R^c$ are as defined in the above [7].

[9] A method according to the above [8] wherein the compound represented by the general formula (6) is pyroglutamine acid.

The method for producing a novel amino acid-modified silane of the present invention is accomplished by reacting an amino-modified silane with a pyroglutamine acid derivative, and accordingly, the amino acid-modified silane can be produced from highly safe inexpensive materials at a high yield. Since the resulting silane has carboxyl group and amino group which realize extremely high hydrophilicity, it can be used as a silane coupling agent, fiber processing agent, powder processing agent, macromolecule modifier, and the like.

Furthermore, the inventors of the present invention found that a novel amino acid group-containing compound can be produced from an aliphatic amine having amino group and a pyroglutamine acid derivative, which are highly safe starting materials, in a convenient manner with no byproducts and at a high yield.

Accordingly, the third aspect of the present invention is an amino acid group-containing compound and a method for producing the amino acid group-containing compound.

[10] An amino acid group-containing compound represented by the following general formula (11):

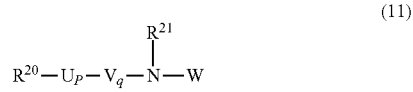
(11)

wherein $R^{20}$ is a monovalent hydrocarbon group containing 6 to 32 carbon atoms, or a monovalent hydrocarbon group containing 8 to 32 carbon atoms having one hydroxy group, $R^{21}$ is hydrogen atom or a monovalent hydrocarbon group containing 1 to 8 carbon atoms, U is sulfur atom, oxygen atom, or an organic group represented by the formula: —$NR^{24}$— wherein $R^{24}$ is hydrogen atom, a monovalent hydrocarbon group containing 1 to 6 carbon atoms, or an organic group represented by the following general formula (12):

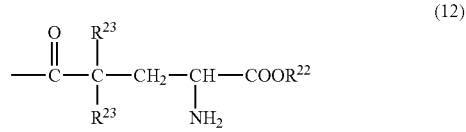
(12)

(wherein $R^{22}$ is hydrogen atom, a monovalent hydrocarbon group containing 1 to 18 carbon atoms, an alkaline metal, or an alkaline earth metal, $R^{23}$ is independently hydrogen atom, hydroxy group, or a monovalent hydrocarbon group containing 1 to 10 carbon atoms optionally containing oxygen atom, sulfur atom, or nitrogen atom), V is a divalent hydrocarbon group containing 2 to 8 carbon atoms, and W is an organic group represented by the general formula (12), p is 0 or 1, and q is 0 or 1.

[11] A method for producing an amino acid group-containing compound of the above [10] comprising the step of reacting an amino group-containing compound represented by the following general formula (13):

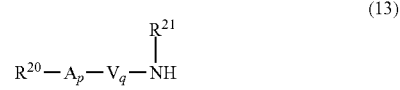
(13)

wherein $R^{20}$, V, $R^{21}$, and q are as defined in the above [10], A is sulfur atom, oxygen atom, or an organic group represented by the formula: —$NR^{25}$— (wherein $R^{25}$ is hydrogen atom or a monovalent hydrocarbon group containing 1 to 6 carbon atoms), and p is 0 or 1 with a compound represented by the following general formula (14):

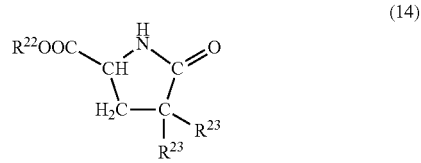
(14)

wherein $R^{22}$ and $R^{23}$ are as defined in the above [10].

[12] A method according to the above [11] wherein the compound represented by the general formula (13) is an aliphatic amine containing 6 to 32 carbon atoms.

[13] A method according to the above [11] wherein the compound represented by the general formula (13) is a higher aliphatic amine containing 12 to 32 carbon atoms.

[14] A method according to the above [11] wherein the compound represented by the general formula (13) is a hydroxy aliphatic amine containing 6 to 32 carbon atoms.

[15] A method according to any one of the above [11] to [14] wherein the compound represented by the general formula (14) is pyroglutamine acid.

This novel amino acid group-containing compound can be produced from highly safe starting materials in a convenient manner at a high yield. This amino acid group-containing compound may be used as a surfactant, and in particular, in a detergent, cosmetic, quasi drug in the field of cosmetics.

DESCRIPTION OF EMBODIMENTS

The amino acid-modified organopolysiloxane of the present invention is an amino acid-modified organopolysiloxane having an amino acid derivative bonded to at least one silicon atom of the organopolysiloxane segment constituting the backbone via an amide bond represented by the following general formula (1):

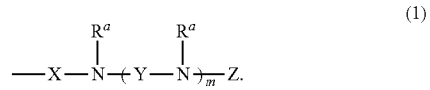

(1)

The organopolysiloxane segment constituting the backbone is not particularly limited and it may have a straight chain, branched or cyclic structure, while the preferred is the straight chain structure.

In the general formula (1), X and Y are independently a divalent hydrocarbon group containing 1 to 10 carbon atoms; m is an integer of 0 to 4; $R^a$ is a group selected from hydrogen atom, a monovalent hydrocarbon group containing 1 to 4 carbon atoms, and an organic group represented by the following general formula (2):

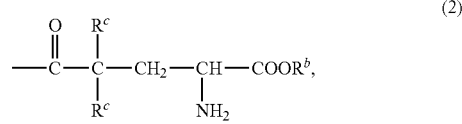

(2)

and Z is an organic group represented by the general formula (2).

In the general formula (2), $R^b$ is hydrogen atom, a monovalent hydrocarbon group containing 1 to 7 carbon atoms, an alkaline metal, or an alkaline earth metal; and $R^c$ is independently hydrogen atom, hydroxy group, or a monovalent hydrocarbon group containing 1 to 10 carbon atoms optionally containing oxygen atom, sulfur atom, or nitrogen atom.

In the general formula (1), the divalent hydrocarbon group containing 1 to 10 carbon atoms represented by X and Y is preferably a straight chain or branched divalent aliphatic hydrocarbon group containing 1 to 10 carbon atoms or a divalent aromatic hydrocarbon group containing 6 to 10 carbon atoms; more preferably an alkylene group containing 1 to 10 carbon atoms, and more preferably 2 to 6 or phenylene group; and even more preferably, ethylene group, trimethylene group, propylene group, butylene group, hexamethylene ring, or phenylene group. Letter m is an integer of 0 to 4, and preferably, an integer of 0 to 3. $R^a$ is a group selected from hydrogen atom, a monovalent hydrocarbon group containing 1 to 4 carbon atoms, and the group represented by the general formula (2), and preferably, a group selected from hydrogen atom, a monovalent saturated aliphatic hydrocarbon group containing 1 to 4 carbon atoms, and the group represented by the general formula (2). More preferably, $R^a$ is hydrogen atom, methyl group, ethyl group, propyl group, butyl group, or the group represented by the general formula (2). Z is the group represented by the general formula (2). In the general formula (2), $R^b$ is hydrogen atom, a monovalent hydrocarbon group containing 1 to 7 carbon atoms, an alkaline metal, or an alkaline earth metal; and the monovalent hydrocarbon group containing 1 to 7 carbon atoms is preferably a monovalent saturated hydrocarbon group containing 1 to 7 carbon atoms such as methyl group, ethyl group, propyl group, butyl group, heptyl group, hexyl group, and heptyl group. Exemplary alkaline metals include lithium, sodium, and potassium, and exemplary alkaline earth metals include beryllium, magnesium, and calcium. $R^b$ is preferably hydrogen atom, methyl group, ethyl group, propyl group, butyl group, benzyl group, an alkaline metal, or an alkaline earth metal, more preferably hydrogen atom, methyl group, ethyl group, sodium, potassium, magnesium, or calcium, and most preferably hydrogen atom. $R^c$ is independently hydrogen atom, hydroxy group, or a monovalent hydrocarbon group containing 1 to 10 carbon atoms optionally containing oxygen atom, sulfur atom, or nitrogen atom. The monovalent hydrocarbon group containing 1 to 10 carbon atoms optionally containing oxygen atom, sulfur atom, or nitrogen atom may be a straight chain or branched monovalent aliphatic hydrocarbon group containing 1 to 10 carbon atoms, a monovalent aromatic hydrocarbon group containing 6 to 10 carbon atoms, or a straight chain or branched monovalent aliphatic saturated hydrocarbon group containing 1 to 10 carbon atoms containing oxygen atom, sulfur atom, or nitrogen atom, or a monovalent aromatic hydrocarbon group containing 6 to 10 carbon atoms containing oxygen atom, sulfur atom, or nitrogen atom; and preferably hydrogen atom, hydroxy group, methyl group, or ethyl group.

The amino acid-modified organopolysiloxane of the present invention may be a compound represented by the average compositional formula (3):

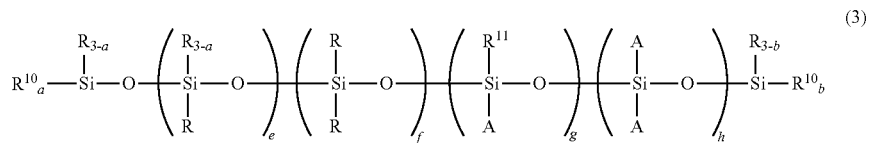

(3)

wherein R is independently a group selected from hydrogen atom, hydroxy group, an alkyl group containing 1 to 30 carbon atoms, a fluoroalkyl group containing 1 to 30 carbon atoms, an aryl group containing 6 to 30 carbon atoms, an aralkyl group containing 7 to 30 carbon atoms. Examples of the alkyl group containing 1 to 30 carbon atoms, the fluoroalkyl group containing 1 to 30 carbon atoms, the aryl group containing 6 to 30 carbon atoms, and the aralkyl group containing 7 to 30 carbon atoms include alkyl groups such as methyl group, ethyl group, propyl group, butyl group, pentyl group, hexyl group, heptyl group, octyl group, nonyl group, decyl group, stearyl group, cyclopentyl group, and cyclohexyl group, aryl groups such as phenyl group and tolyl group, aralkyl groups such as benzyl group and phenethyl group, and fluoroalkyl groups such as trifluoropropyl group and heptadecafluorodecyl group. Of these, the preferred are alkyl groups containing 1 to 15 carbon atoms and phenyl group, and the most preferred is methyl group. $R^{10}$ is an organic group represented by the general formula (1). $R^{11}$ is an organic group selected from $R^{10}$ and R. A is an organopolysiloxane segment represented by the following general formula (4):

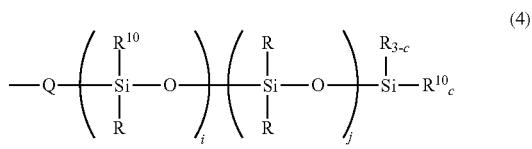

wherein R and $R^{10}$ are as defined above, Q is oxygen atom or a divalent hydrocarbon group containing 1 to 3 carbon atoms, and preferably oxygen atom.

In the formula (3) and general formula (4), a, b, and c are independently an integer of 0 to 3; e is an integer of 0 to 500, and preferably an integer of 1 to 100; f is an integer of 0 to 50,000, and preferably 1 to 4,000; g is an integer of 0 or 1; h is an integer of 0 or 1; i is an integer of 0 to 500, and preferably 0 to 100; j is an integer of 0 to 10,000, and preferably 0 to 3,000; with the proviso that, $1 \leq a+b+c+e+g+i$ when $R^{11}$ is the same as $R^{10}$ and $1 \leq a+b+c+e+i$ when $R^{11}$ is the same as R.

The present invention also provides a method for producing the amino acid-modified organopolysiloxane comprising the step of reacting an amino-modified organopolysiloxane having the amino group bonded to at least one silicon in the organopolysiloxane segment constituting the backbone of the amino-modified organopolysiloxane wherein the amino group is represented by the following general formula (5):

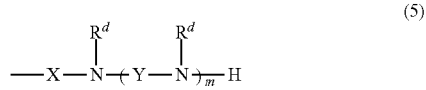

with a compound represented by the following general formula (6):

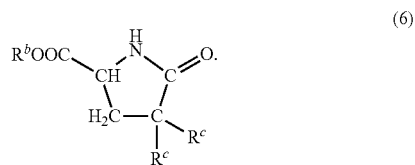

In the general formula (5), X, Y, and m are as defined above, and $R^d$ is hydrogen atom or a monovalent hydrocarbon group containing 1 to 4 carbon atoms, preferably a straight chain or branched aliphatic saturated hydrocarbon containing 1 to 4 carbon atoms, and more preferably hydrogen atom, methyl group, ethyl group, propyl group, or butyl group.

In the general formula (6), $R^b$ and $R^c$ are as defined above, and preferably pyroglutamine acid or sodium pyroglutamate. The compound of the general formula (6) has an asymmetric carbon, and the compound is not particularly limited to any one of the optically active substance and the racemic body.

The amino-modified organopolysiloxane of the present invention is the one represented by the following average compositional formula (7):

wherein R is as defined above for the formula (3), $R^{12}$ is an organic group represented by general formula (5), $R^{13}$ is an organic group selected from $R^{12}$ and R, and $A^1$ is an organopolysiloxane segment represented by the following general formula (8):

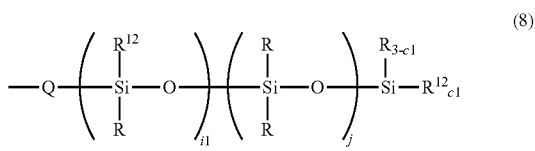

wherein R, $R^{12}$, and Q are as defined above.

In the formula (7) and the general formula (8), a1, b1, and c1 are independently an integer of 0 to 3, e1 is an integer of 0 to 500, and preferably 1 to 100, f is an integer of 0 to 50,000, and preferably 1 to 4,000, g1 is an integer of 0 of 1, h1 is an integer of 0 or 1, i1 is an integer of 0 to 500, and preferably 0 to 100, and j is an integer of 0 to 10,000, and preferably 0 to 3,000 with the proviso that $1 \leq a1+b1+c1+e1+g1+i1$ when $R^{13}$ is $R^{12}$ and $1 \leq a1+b1+c1+e1+i1$ when $R^{13}$ is R.

The amino-modified organopolysiloxane having the amino group bonded to at least one silicon in the organopolysiloxane segment constituting the backbone and the compound represented by the general formula (6) of the present invention reacts in a stoichiometric manner with no need of using the catalyst. These compounds, however, may be used such that 0.3 to 1.5 equivalents, preferably 0.8 to 1.1 equivalents, and more preferably 1.0 equivalent of the compound represented by the general formula (6) is present in relation to 1 equivalent of the amino group in the organopolysiloxane. Content of the amino group in the polysiloxane represented by the general formula (5) may be confirmed by measuring amine equivalent.

The reaction process for producing the amino acid-modified organopolysiloxane of the present invention is preferably conducted at a reaction temperature of 50 to 160° C. More preferably, the reaction is conducted at a reaction temperature of 70 to 100° C. since the reaction at a high temperature may invite coloring of the resulting product by the byproduct formation. The reaction time is not particularly limited. However, the reaction is preferably conducted for 2 to 10 hours, and more preferably for 3 to 5 hours.

While the reaction process for producing the amino acid-modified organopolysiloxane of the present invention proceeds under solventless conditions, the reaction may be conducted in an organic solvent. The organic solvent used is not particularly limited, and exemplary solvents include alcoholic solvents such as methanol, ethanol, propanol, and butanol; ketone solvents such as acetone and methyl ethyl ketone; amide solvents such as N,N-dimethylacetamide, N,N-dimethylformamide, and N-methyl-2-pyrrolidone; and ether solvents such as tetrahydrofuran and 1,4-dioxane. The most preferred are methanol, ethanol, 2-propanol, 1-propanol, and 1-butanol in view of the reaction temperature

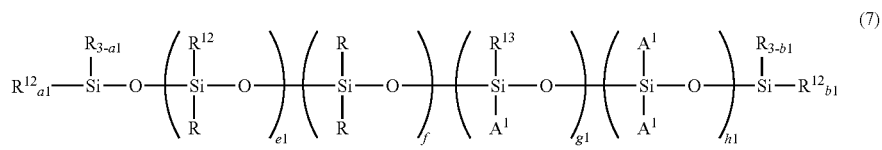

which does not exceed 100° C., and in view of the ease of the solvent removal as well as the safety. Since no byproducts are formed in the production method of the present invention, no purification other than the removal of the solvent is required.

The novel amino acid-modified organopolysiloxane of the present invention may be used for the applications such as cosmetics, powder surface treatment, fiber treatment, coating composition, and resin modification.

Next, the amino acid-modified silane is described.

The amino acid-modified silane of the present invention is the one represented by the following general formula (9):

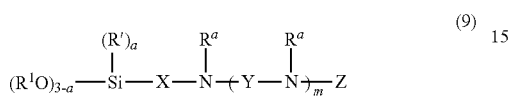

(9)

wherein X and Y are independently a divalent hydrocarbon group containing 1 to 10 carbon atoms; R' is independently a group selected from hydrogen atom, a monovalent alkyl group containing 1 to 30 carbon atoms, a monovalent fluoroalkyl group containing 1 to 30 carbon atoms, a monovalent aryl group containing 6 to 30 carbon atoms, and a monovalent aralkyl group containing 7 to 30 carbon group; $R^1$ is independently hydrogen atom or a monovalent group containing to 1 to 10 carbon atoms; $R^a$ is a group selected from hydrogen atom, a monovalent hydrocarbon group containing 1 to 4 carbon atoms, and a group represented by the following general formula (2):

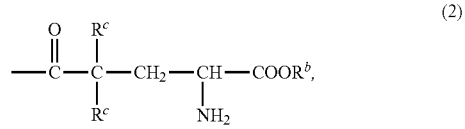

(2)

(wherein $R^b$ is hydrogen atom, a monovalent hydrocarbon group containing 1 to 7 carbon atoms, an alkaline metal, or an alkaline earth metal, $R^c$ is independently hydrogen atom, hydroxy group, or a monovalent hydrocarbon group containing 1 to 10 carbon atoms optionally containing oxygen atom, sulfur atom, or nitrogen atom); a is an integer of 0 to 3; m is an integer of 0 to 4; and Z is an organic group represented by the general formula (2).

More specifically, X, Y, Z, $R^a$, and m are as defined above. R' is independently a group selected from hydrogen atom, hydroxy group, an alkyl group containing 1 to 30 carbon atoms, a fluoroalkyl group containing 1 to 30 carbon atoms, an aryl group containing 6 to 30 carbon atoms, and an aralkyl group containing 7 to 30 carbon atoms. Examples of the alkyl group containing 1 to 30 carbon atoms, the fluoroalkyl group containing 1 to 30 carbon atoms, the aryl group containing 6 to 30 carbon atoms, and the aralkyl group containing 7 to 30 carbon atoms include alkyl groups such as methyl group, ethyl group, propyl group, butyl group, pentyl group, hexyl group, heptyl group, octyl group, nonyl group, decyl group, stearyl group, cyclopentyl group, and cyclohexyl group, aryl groups such as phenyl group and tolyl group, aralkyl groups such as benzyl group and phenethyl group, and fluoroalkyl groups such as trifluoropropyl group and heptadecafluorodecyl group. Of these, the preferred are alkyl groups containing 1 to 15 carbon atoms and phenyl group, and the most preferred is methyl group. $R^1$ is independently hydrogen atom or a monovalent group containing 1 to 10 carbon atoms, preferably a straight chain or branched monovalent saturated aliphatic hydrocarbon group containing 1 to 10 carbon atoms or a monovalent aromatic hydrocarbon group containing 6 to 10 carbon atoms, more preferably hydrogen atom, methyl group, ethyl group, propyl group, butyl group, heptyl group, or hexyl group, and most preferably methyl group or ethyl group. Letter a is an integer of 0 to 3, and preferably 0 or 1.

The present invention also provides a method for producing an amino acid-modified silane comprising the step of reacting an amino-modified silane having an amino group bonded thereto represented by the following general formula (10):

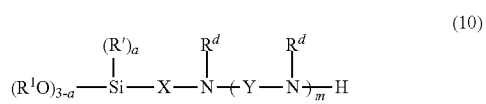

(10)

with a compound represented by the general formula (6):

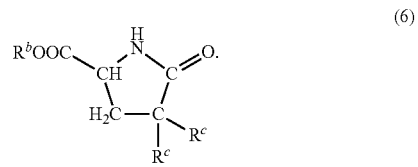

(6)

In the general formula (10), R', $R^1$, X, Y, and m are as defined above, and $R^d$ is a group selected from hydrogen atom, a monovalent hydrocarbon group containing 1 to 4 carbon atoms, and a group represented by the general formula (2), and preferably hydrogen atom, methyl group, ethyl group, propyl group, butyl group, or the general formula (2).

Examples of the amino-modified silanes include
3-aminopropyltrimethylsilane,
3-aminopropyldimethylmethoxysilane,
3-aminopropyldimethoxymethylsilane,
3-aminopropyltrimethoxysilane,
3-aminopropyldimethylethoxysilane,
3-aminopropyldiethoxymethylsilane,
3-aminopropyltriethoxysilane,
3-(2-aminoethylaminopropyl)trimethylsilane,
3-(2-aminoethylaminopropyl)dimethylmethoxysilane,
3-(2-aminoethylaminopropyl)dimethoxymethylsilane,
3-(2-aminoethylaminopropyl)trimethoxysilane,
3-(2-aminoethylaminopropyl)dimethylethoxysilane,
3-(2-aminoethylaminopropyl)diethoxymethylsilane,
3-(2-aminoethylaminopropyl)triethoxysilane,
3-aminopropyldi(trimethylsiloxy)methylsilane, aminomethyltrimethylsilane, and
2-aminoethylaminomethyltrimethylsilane.

The general formula (6) is as described above.

The amino-modified silane having an amino group bonded thereto represented by the general formula (10) and the compound represented by the general formula (6) of the present invention reacts in a stoichiometric manner. These compounds, however, may be used such that 0.3 to 1.5 equivalents, preferably 0.8 to 1.1 equivalents, and more preferably 1.0 equivalent of the compound represented by the general formula (6) is present in relation to 1 equivalent of the amino group in the silane.

The reaction process for producing the amino acid-modified silane of the present invention is preferably conducted at a reaction temperature of 0 to 160° C. More preferably, the reaction is conducted at a reaction temperature of 20 to 80° C. since the reaction at a high temperature may result coloring of the resulting product by the byproduct formation. The reaction time is not particularly limited. However, the reaction is preferably conducted for 1 to 10 hours, and more preferably for 3 to 5 hours.

While the reaction process for producing the amino acid-modified silane of the present invention proceeds under solventless conditions, the reaction may be conducted in an organic solvent. The organic solvent used is not particularly limited, and exemplary solvents include alcoholic solvents such as methanol, ethanol, propanol, and butanol; ketone solvents such as acetone, and methyl ethyl ketone; amide solvents such as N,N-dimethyl acetamide, N,N-dimethylformamide, and N-methyl-2-pyrrolidone; and ether solvents such as tetrahydrofuran and 1,4-dioxane. The most preferred are methanol, ethanol, 2-propanol, 1-propanol, and 1-butanol. The reaction process of the present invention proceeds in a stoichiometric manner without generating byproducts, and further purification is unnecessary. The reaction product may be stored in the solvent used for the reaction without any further processing.

The novel amino acid-modified silane of the present invention is useful, for example, as a silane coupling agent, fiber processing agent, powder processing agent, and macromolecule modifier.

The present invention also provides an amino acid group-containing compound represented by the following general formula (11):

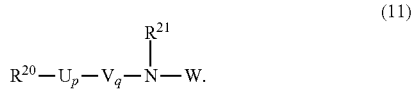

(11)

In the general formula (11), $R^{20}$ is a monovalent hydrocarbon group containing 6 to 32 carbon atoms, or a monovalent hydrocarbon group containing 8 to 32 carbon atoms having one hydroxy group. The monovalent hydrocarbon group containing 6 to 32 carbon atoms is preferably a straight chain or branched monovalent aliphatic hydrocarbon group containing 6 to 32 carbon atoms or an aromatic hydrocarbon group containing 6 to 32 carbon atoms, and more preferably a straight chain or branched monovalent aliphatic saturated hydrocarbon group containing 12 to 32 carbon atoms. The monovalent hydrocarbon group containing 8 to 32 carbon atoms having one hydroxy group is preferably a straight chain or branched monovalent aliphatic hydrocarbon group containing 8 to 32 carbon atoms having one hydroxy group or an aromatic hydrocarbon group containing 8 to 32 carbon atoms having one hydroxy group, and more preferably a straight chain or branched monovalent aliphatic saturated hydrocarbon group containing 10 to 32 carbon atoms having one hydroxy group. $R^{21}$ is hydrogen atom or a monovalent hydrocarbon group containing 1 to 8 carbon atoms, which is preferably, more preferably hydrogen atom, a straight chain or branched monovalent aliphatic hydrocarbon group containing 1 to 8 carbon atoms, more preferably hydrogen atom, a straight chain or branched monovalent aliphatic saturated hydrocarbon group containing 1 to 8 carbon atoms, and most preferably hydrogen atom, methyl group, ethyl group, or propyl group. U is sulfur atom, oxygen atom, or an organic group represented by the formula: —$NR^{24}$— wherein $R^{24}$ is hydrogen atom, a monovalent hydrocarbon group containing 1 to 6 carbon atoms, or an organic group represented by the following general formula (12):

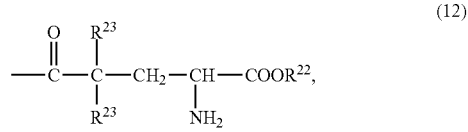

(12)

preferably hydrogen atom, a straight chain or branched monovalent aliphatic saturated hydrocarbon group containing 1 to 6 carbon atom or an organic group represented by the general formula (12), and more preferably, hydrogen atom, methyl group, ethyl group, or an organic group represented by the general formula (12). V is a divalent hydrocarbon group containing 2 to 8 carbon atoms, which is preferably a straight chain or branched divalent aliphatic hydrocarbon group containing 2 to 8 carbon atoms, more preferably a straight chain or branched divalent aliphatic saturated hydrocarbon group containing 2 to 8 carbon atoms, and most preferably a straight chain divalent aliphatic saturated hydrocarbon group containing 2 to 4 carbon atoms. W is an organic group represented by the general formula (12), p is 0 or 1 and q is 0 or 1, and preferably, p is 0 and q is 0.

In the general formula (12), $R^{22}$ is hydrogen atom, a monovalent hydrocarbon group containing 1 to 18 carbon atoms, an alkaline metal, or an alkaline earth metal; preferably hydrogen atom, a straight chain or branched monovalent aliphatic hydrocarbon group containing 1 to 18 carbon atoms, an alkaline metal, or an alkaline earth metal; more preferably hydrogen atom, a monovalent aliphatic saturated hydrocarbon group containing 1 to 18 carbon atoms, an alkaline metal, or an alkaline earth metal; and most preferably hydrogen atom, a straight chain monovalent aliphatic saturated hydrocarbon group containing 1 to 12 carbon atoms, sodium, potassium, magnesium, or calcium. $R^{23}$ is independently hydrogen atom, hydroxy group, or a monovalent hydrocarbon group containing 1 to 10 carbon atoms optionally containing oxygen atom, sulfur atom, or nitrogen atom; preferably hydrogen atom, hydroxy group, a straight chain or branched monovalent aliphatic hydrocarbon group containing 1 to 10 carbon atoms, a monovalent aromatic hydrocarbon group containing 6 to 10 carbon atoms, a straight chain or branched monovalent aliphatic saturated hydrocarbon group containing 1 to 10 carbon atoms optionally containing oxygen atom, sulfur atom, or nitrogen atom, or a monovalent aromatic hydrocarbon group containing 6 to 10 carbon atoms optionally containing oxygen atom, sulfur atom, or nitrogen atom; more preferably hydrogen atom, hydroxy group, methyl group, ethyl group, propyl group, butyl group, heptyl group, or hexyl group; and most preferably hydrogen atom.

The present invention also provides a method for producing an amino acid group-containing compound comprising the step of reacting an amino group-containing compound represented by the following general formula (13):

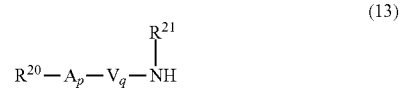

(13)

with a compound represented by the following general formula (14):

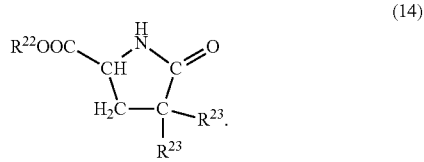

(14)

In the general formula (13), $R^{20}$, V, $R^{21}$, and q are as defined above, and A is sulfur atom, oxygen atom, or an organic group represented by the formula: —$NR^{25}$— (wherein $R^{25}$ is hydrogen atom or a monovalent hydrocarbon group containing 1 to 6 carbon atoms), and p is 0 or 1.

In the general formula (14), $R^{22}$ and $R^{23}$ are as defined above. The compound represented by the general formula (14) is preferably pyroglutamine acid or sodium pyroglutamate which is commercially available, and more preferably pyroglutamine acid. The compound represented by the general formula (14) has an asymmetric carbon, and the compound is not particularly limited to any one of the optically active substance and the racemic body.

Examples of the aliphatic amine containing 6 to 32 carbon atoms of the present invention include hexylamine, heptylamine, octylamine, 1,5-dimethyl hexylamine, nonylamine, decylamine, dodecylamine, tetradecylamine, pentadecylamine, hexadecylamine, 9-hexadecenylamine, heptadecylamine, octadecylamine, 9-octadecenylamine, 11-octadecenylamine, 9,12-octadecadienylamine, nonadecylamine, eicocylamine, docosylamine, tetradocosylamine, hexadococylamine, octadocosylamine, 3-(2-ethylhexyloxy)propylamine, and derivatives of such amine prepared by transformation to the corresponding secondary amine.

Examples of the higher aliphatic amine containing 12 to 32 carbon atoms of the present invention include dodecylamine, tetradecylamine, pentadecylamine, hexadecylamine, 9-hexadecenylamine, heptadecylamine, octadecylamine, 9-octadecenylamine, 11-octadecenylamine, 9,12-octadecadienylamine, nonadecylamine, eicosylamine, docosylamine, tetradococylamine, hexadococylamine, octadococylamine, and derivatives of such amine prepared by transformation to the corresponding secondary amine.

Examples of the hydroxy aliphatic amine containing 8 to 32 carbon atoms of the present invention include amines such as 12-amino-1-dodecanol, 12-hydroxy octadecylamine, and derivatives of such amine prepared by transformation to the corresponding secondary amine.

The compound represented by the general formula (13) and the compound represented by the general formula (14) of the present invention reacts in a stoichiometric manner. These compounds, however, may be used such that 0.3 to 1.5 equivalents, preferably 0.8 to 1.1 equivalents, and more preferably 1.0 equivalent of the compound represented by the general formula (14) is present in relation to 1 equivalent of the amino group in the compound represented by the general formula (13).

The reaction process of the present invention is preferably conducted at a reaction temperature of 1 to 160° C. More preferably, the reaction is conducted at a reaction temperature of 20 to 80° C. since the reaction at a high temperature may invite coloring of the resulting product. The reaction time is not particularly limited. However, the reaction is preferably conducted for 1 to 10 hours, and more preferably for 3 to 5 hours.

While the reaction process of the present invention proceeds under solventless conditions, the reaction may be conducted in an organic solvent.

The organic solvent used is not particularly limited, and exemplary solvents include alcoholic solvents such as methanol, ethanol, propanol, and butanol; ketone solvents such as acetone, and methyl ethyl ketone; amide solvents such as N,N-dimethyl acetamide, N,N-dimethylformamide, and N-methyl-2-pyrrolidone; and ether solvents such as tetrahydrofuran and 1,4-dioxane. The most preferred are methanol, ethanol, 2-propanol, 1-propanol, and 1-butanol. The reaction process of the present invention proceeds in a stoichiometric manner without generating byproducts, and further purification is unnecessary. When complete removal of excessive ingredients remaining in the reaction system is necessary because of the amount of the compounds of the general formula (13) and the general formula (14) used, the reaction system may be washed with an adequate solvent such as water, methanol, or toluene.

The amino acid group-containing compound of the present invention may be used as a surfactant, and in particular, as a surfactant in the field of cosmetics including detergents, cosmetics, and quasi drugs.

EXAMPLES

Next, the present invention is described in further detail by referring to the Examples, which by no means limit the scope of the present invention.

Example 1

A reaction vessel was charged with 180 parts by weight of organopolysiloxane represented by the following average compositional formula (1):

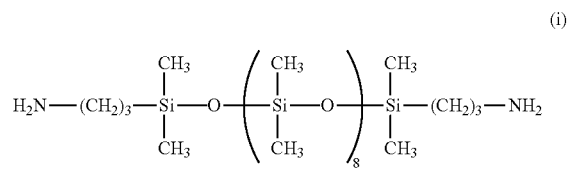

having an amine equivalent of 410 g/mol, 100 parts by weight of methanol, and 56 parts by weight of DL-pyroglutamine acid, and the mixture was stirred at 80° C. for 4 hours.

The resulting reaction mixture was stripped at 90° C. under reduced pressure to remove the solvent, and 224 parts by weight of white wax-like solid was obtained at a yield of 95%. Results of the $^{13}$C-NMR shown in Table 1, below, and absorption at 1687 cm$^{-1}$ (from amide bond) in the measurement of IR spectrum confirmed that the resulting product was an amino acid-modified organopolysiloxane in which

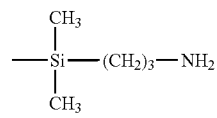

at both ends the formula (i) had been respectively converted to the following formula (ii):

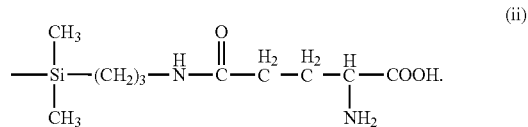

TABLE 1

| $^{13}$C-NMR (CDCl$_3$) |
|---|
| 0~1.4 ppm (Si—CH$_3$) |
| 15.0 ppm (Si—CH$_2$—CH$_2$—CH$_2$—) |

TABLE 1-continued $^{13}$C-NMR (CDCl$_3$)

30.5 ppm (Si—CH$_2$—$\underline{C}$H$_2$—CH$_2$—)
42.2 ppm (Si—CH$_2$—CH$_2$—$\underline{C}$H$_2$—)
178.5 ppm (—NH—$\underline{C}$O—)
22.0 ppm (—CO—$\underline{C}$H$_2$—CH$_2$—)
25.6 ppm (—CO—CH$_2$—$\underline{C}$H$_2$—)
58.5 ppm [—$\underline{C}$H(NH$_2$)(COOH)]
179.4 ppm (—$\underline{C}$OOH)

Example 2

A reaction vessel was charged with 200 parts by weight of organopolysiloxane represented by the following average compositional formula (iii):

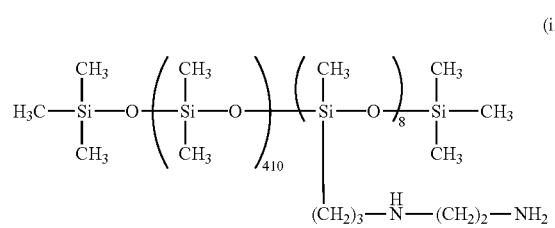

(iii)

having an amine equivalent of 1,910 g/mol, 150 parts by weight of ethanol, and 7 parts by weight of L-pyroglutamine acid, and the mixture was stirred at 80° C. for 5 hours.

The resulting reaction mixture was stripped at 90° C. under reduced pressure to remove the solvent, and 194 parts by weight of highly viscous colorless transparent liquid was obtained at a yield of 94%. Results of the $^{13}$C-NMR shown in Table 2, below, and absorption at 1687 cm$^{-1}$ (from amide bond) in the measurement of IR spectrum confirmed that the resulting product was an amino acid-modified organopolysiloxane in which

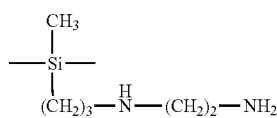

in the formula (iii) had been respectively converted to the following formula (iv):

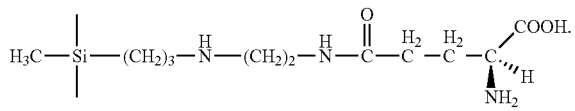

(iv)

TABLE 2

$^{13}$C-NMR (CDCl$_3$)

0~1.4 ppm (Si—$\underline{C}$H$_3$)
15.2 ppm (Si—$\underline{C}$H$_2$—CH$_2$—CH$_2$—)
27.5 ppm (Si—CH$_2$—$\underline{C}$H$_2$—CH$_2$—)
44.5 ppm (Si—CH$_2$—CH$_2$—$\underline{C}$H$_2$—)
45.2 ppm (NH—$\underline{C}$H$_2$—CH$_2$—)

TABLE 2-continued $^{13}$C-NMR (CDCl$_3$)

42.3 ppm (NH—CH$_2$—$\underline{C}$H$_2$—)
178.5 ppm (—NH—$\underline{C}$O—)
22.1 ppm (—CO—$\underline{C}$H$_2$—CH$_2$—)
25.6 ppm (—CO—CH$_2$—$\underline{C}$H$_2$—)
58.5 ppm [—$\underline{C}$H(NH$_2$)(COOH)]
179.4 ppm (—$\underline{C}$OOH)

Example 3

A reaction vessel was charged with 250 parts by weight of organopolysiloxane represented by the following average compositional formula (v):

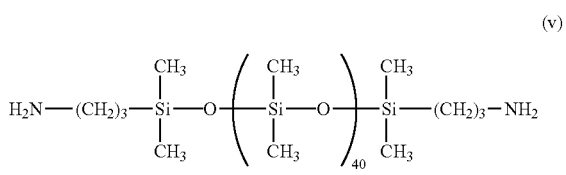

(v)

having an amine equivalent of 1,490 g/mol and 26 parts by weight of ethyl DL-pyroglutamate, and the mixture was stirred at 120° C. for 5 hours to obtain 267 parts by weight of the product at a yield of 94%.

The resulting product was pale yellow transparent liquid having an amino equivalent of 1,630 g/mol. Results of the $^{13}$C-NMR shown in Table 3, below, and absorption at 1687 cm$^{-1}$ (from amide bond) in the measurement of IR spectrum confirmed that the resulting product was an amino acid-modified organopolysiloxane in which

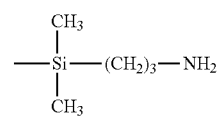

at both ends of the formula (v) had been respectively converted to the following formula (vi):

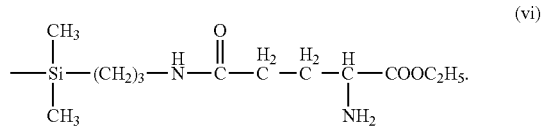

(vi)

TABLE 3

$^{13}$C-NMR (CDCl$_3$)

0~1.4 ppm (Si—$\underline{C}$H$_3$)
15.0 ppm (Si—$\underline{C}$H$_2$—CH$_2$—CH$_2$—)
30.5 ppm (Si—CH$_2$—$\underline{C}$H$_2$—CH$_2$—)
42.2 ppm (Si—CH$_2$—CH$_2$—$\underline{C}$H$_2$—)
178.5 ppm (—NH—$\underline{C}$O—)
22.0 ppm (—CO—$\underline{C}$H$_2$—CH$_2$—)
25.7 ppm (—CO—CH$_2$—$\underline{C}$H$_2$—)
58.2 ppm [—$\underline{C}$H(NH$_2$)(COOCH$_2$CH$_3$)]
174.2 ppm (—$\underline{C}$OOCH$_2$CH$_3$)
59.0 ppm (—COO$\underline{C}$H$_2$CH$_3$)
13.4 ppm (—COOCH$_2$$\underline{C}$H$_3$)

Example 4

A reaction vessel was charged with 300 parts by weight of organopolysiloxane represented by the following average compositional formula (vii):

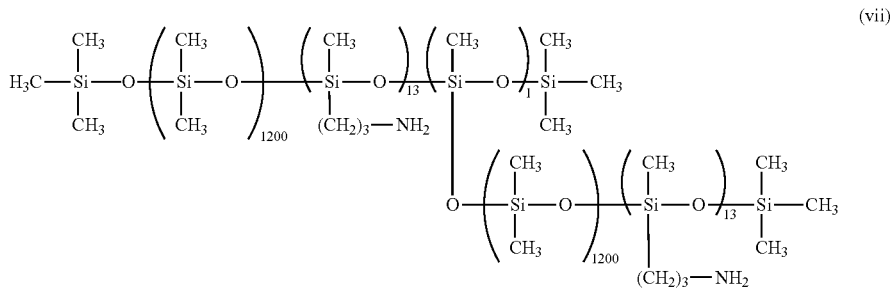

(vii)

having an amine equivalent of 7,250 g/mol, 120 parts by weight of 2-propanol, and 6 parts by weight of DL-pyroglutamate, and the mixture was stirred at 95° C. for 5 hours.

The resulting reaction mixture was stripped at 100° C. under reduced pressure to remove the solvent, and 293 parts by weight of highly viscous colorless transparent liquid was obtained at a yield of 95%. Results of the $^{13}$C-NMR shown in Table 4, below, and absorption at 1685 cm$^{-1}$ (from amide bond) in the measurement of IR spectrum confirmed that the resulting product was an amino acid-modified organopolysiloxane in which

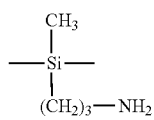

in the formula (vii) had been respectively converted to the following formula (viii):

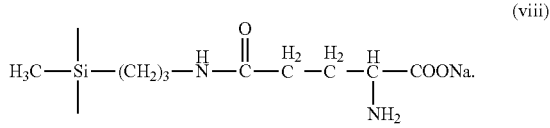

(viii)

TABLE 4

| $^{13}$C-NMR (CDCl$_3$) |
| --- |
| 0~1.4 ppm (Si—$\underline{C}$H$_3$) |
| 15.0 ppm (Si—$\underline{C}$H$_2$—CH$_2$—CH$_2$—) |
| 30.5 ppm (Si—CH$_2$—$\underline{C}$H$_2$—CH$_2$—) |
| 42.2 ppm (Si—CH$_2$—CH$_2$—$\underline{C}$H$_2$—) |
| 178.5 ppm (—NH—$\underline{C}$O—) |
| 22.0 ppm (—CO—$\underline{C}$H$_2$—CH$_2$—) |
| 25.7 ppm (—CO—CH$_2$—$\underline{C}$H$_2$—) |
| 58.3 ppm [—$\underline{C}$H(NH$_2$)(COONa)] |
| 179.9 ppm (—$\underline{C}$OONa) |

Example 5

A reaction vessel was charged with 350 parts by weight of organopolysiloxane represented by the following average compositional formula (ix):

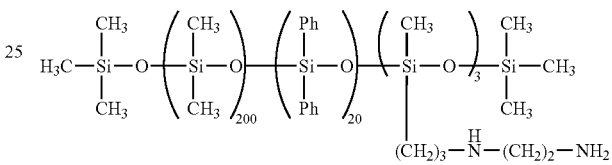

(ix)

having an amine equivalent of 3,230 g/mol, 200 parts by weight of n-butanol, and 14 parts by weight of DL-pyroglutamine acid, and the mixture was stirred at 95° C. for 5 hours.

The resulting reaction mixture was stripped at 120° C. under reduced pressure to remove the solvent, and 345 parts by weight of highly viscous colorless transparent liquid was obtained at a yield of 95%. Results of the $^{13}$C-NMR shown in Table 5, below, and absorption at 1685 cm$^{-1}$ (from amide bond) in the measurement of IR spectrum confirmed that the resulting product was an amino acid-modified organopolysiloxane in which

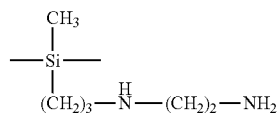

in the formula (ix) had been respectively converted to the following formula (x):

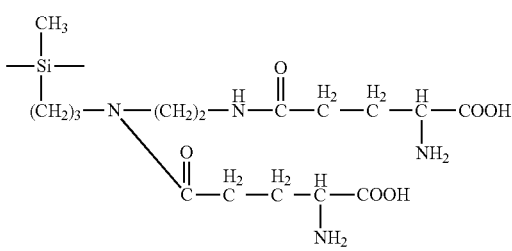

(x)

TABLE 5

| $^{13}$C-NMR (CDCl$_3$) |
|---|
| 0~1.4 ppm (Si—$\underline{C}$H$_3$) |
| 128.2~135.1 ppm (Si—$\underline{Ph}$) |
| 15.5 ppm (Si—$\underline{C}$H$_2$—CH$_2$—CH$_2$—) |
| 28.8 ppm (Si—CH$_2$—$\underline{C}$H$_2$—CH$_2$—) |
| 46.9 ppm (Si—CH$_2$—CH$_2$—$\underline{C}$H$_2$—) |
| 47.1 ppm (N—$\underline{C}$H$_2$—CH$_2$—) |
| 42.7 ppm (N—CH$_2$—$\underline{C}$H$_2$—) |
| 179.2 ppm (—NH—$\underline{C}$O—) |
| 179.2 ppm (—N—$\underline{C}$O—) |
| 21.5 ppm (—CO—$\underline{C}$H$_2$—CH$_2$—) |
| 25.2 ppm (—CO—CH$_2$—$\underline{C}$H$_2$—) |
| 57.9 ppm [—$\underline{C}$H(NH$_2$)(COOH)] |
| 179.9 ppm (—$\underline{C}$OOH) |

Example 6

A reaction vessel was charged with 80 parts by weight of organopolysiloxane represented by the following average compositional formula (xi):

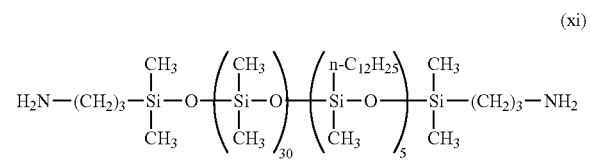

(xi)

having an amine equivalent of 600 g/mol, 18 parts by weight of 4,4-dimethyl pyroglutamine acid, and 15 parts by weight of 2-propanol, and the mixture was stirred at 95° C. for 5 hours.

The resulting reaction mixture was stripped at 100° C. under reduced pressure to remove the solvent, and 94 parts by weight of highly viscous colorless transparent liquid was obtained at a yield of 94%. Results of the $^{13}$C-NMR shown in Table 6, below, and absorption at 1683 cm$^{-1}$ (from amide bond) in the measurement of IR spectrum confirmed that the resulting product was an amino acid-modified organopolysiloxane in which

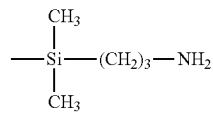

at both ends of the formula (xi) had been respectively converted to the following formula (xii):

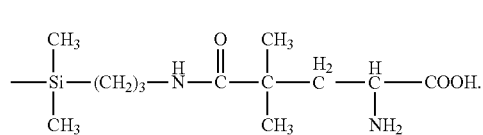

(xii)

TABLE 6

| $^{13}$C-NMR (CDCl$_3$) |
|---|
| 0~33.4 ppm [Si—$\underline{C}$H$_3$ Si—($\underline{C}$H$_2$)$_{11}$—$\underline{C}$H$_3$] |
| 15.2 ppm (Si—$\underline{C}$H$_2$—CH$_2$—CH$_2$—) |

TABLE 6-continued

| $^{13}$C-NMR (CDCl$_3$) |
|---|
| 30.8 ppm (Si—CH$_2$—$\underline{C}$H$_2$—CH$_2$—) |
| 42.5 ppm (Si—CH$_2$—CH$_2$—$\underline{C}$H$_2$—) |
| 179.7 ppm (—NH—$\underline{C}$O—) |
| 35.6 ppm (—CO—$\underline{C}$(CH$_3$)$_2$—CH$_2$—) |
| 22.4 ppm (—CO—C($\underline{C}$H$_3$)$_2$—CH$_2$—) |
| 39.8 ppm (—CO—C(CH$_3$)$_2$—$\underline{C}$H$_2$—) |
| 57.2 ppm [—$\underline{C}$H(NH$_2$)(COOH)] |
| 179.2 ppm (—$\underline{C}$OOH) |

Example 7

A reaction vessel was charged with 200 parts by weight of 3-aminopropyltrimethylsilane and 197 parts by weight of DL-pyroglutamine acid, and the mixture was stirred at 100° C. for 3 hours.

After cooling, 385 parts by weight of white solid was obtained at a yield of 97%. Results of the $^{13}$C-NMR shown in Table 7, below, and absorption at 1685 cm$^{-1}$ (from amide bond) in the measurement of IR spectrum confirmed that the resulting product was the amino acid-modified silane represented by following formula:

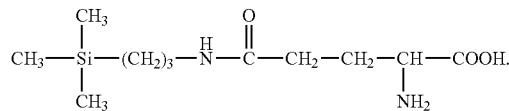

TABLE 7

| $^{13}$C-NMR (CDCl$_3$) |
|---|
| 0.4 ppm (Si—$\underline{C}$H$_3$) |
| 7.4 ppm (Si—$\underline{C}$H$_2$—CH$_2$—CH$_2$—) |
| 19.7 ppm (Si—CH$_2$—$\underline{C}$H$_2$—CH$_2$—) |
| 42.0 ppm (Si—CH$_2$—CH$_2$—$\underline{C}$H$_2$—) |
| 178.8 ppm (—NH—$\underline{C}$O—) |
| 22.5 ppm (—CO—$\underline{C}$H$_2$—CH$_2$—) |
| 25.1 ppm (—CO—CH$_2$—$\underline{C}$H$_2$—) |
| 58.5 ppm (—$\underline{C}$H(NH$_2$)(COOH)] |
| 179.4 ppm (—$\underline{C}$OOH) |

Example 8

A reaction vessel was charged with 170 parts by weight of 3-(2-aminoethylaminopropyl)diethoxymethylsilane, 50 parts by weight of ethanol, and 93 parts by weight of L-pyroglutamine acid, and the mixture was stirred at 30° C. for 4 hours.

To the resulting reaction mixture, 60 parts by weight of ethanol was added to obtain a colorless transparent 50% by weight ethanol solution. Results of the $^{13}$C-NMR shown in Table 8, below, and absorption at 1687 cm$^{-1}$ (from amide bond) in the measurement of IR spectrum confirmed that the resulting product was an amino acid-modified silane represented by the following formula:

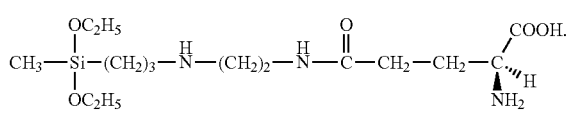

TABLE 8

| $^{13}$C-NMR (CDCl$_3$) |
|---|
| 4.6 ppm (Si—$\underline{C}$H$_3$) |
| 58.2 ppm (Si—O$\underline{C}$H$_2$CH$_3$) |
| 18.3 ppm (Si—OCH$_2$$\underline{C}$H$_3$) |
| 6.8 ppm (Si—$\underline{C}$H$_2$—CH$_2$—CH$_2$—) |
| 16.4 ppm (Si—CH$_2$—$\underline{C}$H$_2$—CH$_2$—) |
| 45.5 ppm (Si—CH$_2$—CH$_2$—$\underline{C}$H$_2$—) |
| 46.5 ppm (NH—$\underline{C}$H$_2$—CH$_2$—) |
| 43.3 ppm (NH—CH$_2$—$\underline{C}$H$_2$—) |
| 178.3 ppm (—NH—$\underline{C}$O—) |
| 22.0 ppm (—CO—$\underline{C}$H$_2$—CH$_2$—) |
| 25.5 ppm (—CO—CH$_2$—$\underline{C}$H$_2$—) |
| 58.5 ppm [—$\underline{C}$H(NH$_2$)(COOH)] |
| 179.4 ppm (—$\underline{C}$OOH) |

Example 9

A reaction vessel was charged with 500 parts by weight of 3-aminopropyloctyldiethoxysilane, 320 parts by weight of ethyl DL-4,4-dimethyl-5-pyrrolidone-2-carboxylate, and 120 parts by weight of ethanol, and the mixture was stirred at 50° C. for 3 hours.

To the resulting reaction mixture, 426 parts by weight of ethanol was added to obtain a colorless transparent 60% by weight ethanol solution. Results of the $^{13}$C-NMR shown in Table 9, below, and absorption at 1685 cm$^{-1}$ (from amide bond) in the measurement of IR spectrum confirmed that the resulting product was an amino acid-modified silane represented by the following formula:

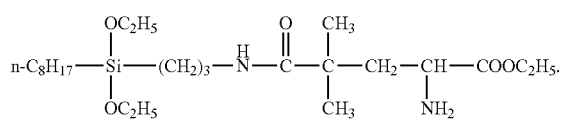

TABLE 9

| $^{13}$C-NMR (CDCl$_3$) |
|---|
| 11.2~33.6 ppm (Si—($\underline{C}$H$_2$)$_7$—$\underline{C}$H$_3$) |
| 58.0 ppm (Si—O$\underline{C}$H$_2$CH$_3$) |
| 18.1 ppm (Si—OCH$_2$$\underline{C}$H$_3$) |
| 7.7 ppm (Si—$\underline{C}$H$_2$—CH$_2$—CH$_2$—) |
| 19.9 ppm (Si—CH$_2$—$\underline{C}$H$_2$—CH$_2$—) |
| 43.8 ppm (Si—CH$_2$—CH$_2$—$\underline{C}$H$_2$—) |
| 179.9 ppm (—NH—$\underline{C}$O—) |
| 35.5 ppm (—CO—$\underline{C}$(CH$_3$)$_2$—CH$_2$—) |
| 22.7 ppm (—CO—C($\underline{C}$H$_3$)$_2$—CH$_2$—) |
| 40.1 ppm (—CO—C(CH$_3$)$_2$—$\underline{C}$H$_2$—) |
| 56.8 ppm [—$\underline{C}$H(NH$_2$)(COOCH$_2$CH$_3$)] |
| 174.0 ppm (—$\underline{C}$OOCH$_2$CH$_3$) |
| 58.6 ppm (—COO$\underline{C}$H$_2$CH$_3$) |
| 13.5 ppm (—COOCH$_2$$\underline{C}$H$_3$) |

Example 10

A reaction vessel was charged with 60 parts by weight of 3-(2-aminoethylaminopropyl)trimethoxysilane, 50 parts by weight of methanol, and 81 parts by weight of sodium DL-pyroglutamate, and the mixture was stirred at 30° C. for 4 hours.

To the resulting reaction mixture, 60 parts by weight of methanol was added to obtain a colorless transparent 30% by weight ethanol solution. Results of the $^{13}$C-NMR shown in Table 10, below, and absorption at 1687 cm$^{-1}$ (from amide bond) in the measurement of IR spectrum confirmed that the resulting product was an amino-modified silane represented by the following formula:

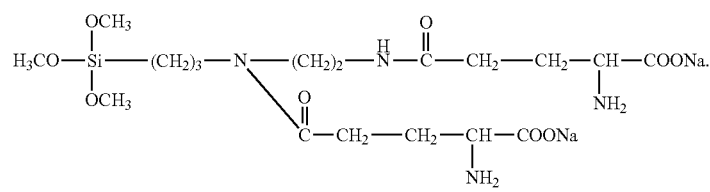

TABLE 10

| $^{13}$C-NMR (CDCl$_3$) |
|---|
| 50.2 ppm (Si—O—$\underline{C}$H$_3$) |
| 6.2 ppm (Si—$\underline{C}$H$_2$—CH$_2$—CH$_2$—) |
| 19.8 ppm (Si—CH$_2$—$\underline{C}$H$_2$—CH$_2$—) |
| 50.5 ppm (Si—CH$_2$—CH$_2$—$\underline{C}$H$_2$—) |
| 45.4 ppm (N—$\underline{C}$H$_2$—CH$_2$—) |
| 36.5 ppm (N—CH$_2$—$\underline{C}$H$_2$—) |
| 179.2 ppm (—N—$\underline{C}$O—) |
| 25.5 ppm (—CO—$\underline{C}$H$_2$—CH$_2$—) |
| 30.2 ppm (—CO—CH$_2$—$\underline{C}$H$_2$—) |
| 179.2 ppm (—NH—$\underline{C}$O—) |
| 58.0 ppm [—$\underline{C}$H(NH$_2$)(COONa)] |
| 179.5 ppm (—$\underline{C}$OONa) |

Example 11

A reaction vessel was charged with 200 parts by weight of octadecylamine, 95 parts by weight of DL-pyroglutamine acid, and 80 parts by weight of ethanol, and the mixture was stirred at 75° C. for 5 hours. The resulting reaction mixture was stripped at 90° C. under reduced pressure to remove the ethanol, and 271 parts by weight of white solid was obtained at a yield of 92%. Results of the $^{13}$C-NMR shown in Table 11, below, and absorption at 1685 cm$^{-1}$ (from amide bond) in the measurement of IR spectrum confirmed that the resulting product was an amino acid compound represented by the formula:

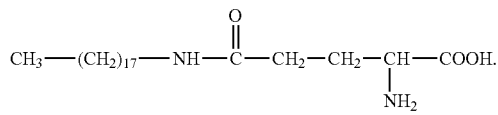

TABLE 11

| $^{13}$C-NMR (CDCl$_3$) |
|---|
| 14.1 ppm (—$\underline{C}$H$_3$) |
| 22~31.9 ppm [—($\underline{C}$H$_2$)$_{16}$—] |
| 39.6 ppm (—$\underline{C}$H$_2$—NH—) |
| 178.5 ppm (—NH—$\underline{C}$O—) |
| 25.5 ppm (—CO—$\underline{C}$H$_2$—CH$_2$—) |
| 28.1 ppm (—CO—CH$_2$—$\underline{C}$H$_2$—) |
| 58.4 ppm [—$\underline{C}$H(NH$_2$)(COOH)] |
| 179.5 ppm (—$\underline{C}$OOH) |

Example 12

A reaction vessel was charged with 150 parts by weight of 1,5-dimethylhexylamine and 175 parts by weight sodium DL-pyroglutaminate, and the mixture was stirred at 140° C. for 5 hours. After cooling, 312 parts by weight of pale yellow solid was obtained at a yield of 94%. Results of the $^{13}$C-NMR shown in Table 12, below, and absorption at 1685 cm$^{-1}$ (from amide bond) in the measurement of IR spectrum confirmed that the resulting product was the amino acid compound represented by following formula:

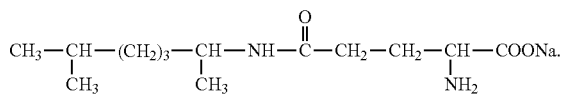

TABLE 12

| $^{13}$C-NMR (CDCl$_3$) |
|---|
| 22.5~44.3 ppm ($\underline{C}$H, —$\underline{C}$H$_2$—, —$\underline{C}$H$_3$) |
| 178.5 ppm (—NH—$\underline{C}$O—) |
| 25.5 ppm (—CO—$\underline{C}$H$_2$—CH$_2$—) |
| 28.1 ppm (—CO—CH$_2$—$\underline{C}$H$_2$—) |
| 58.4 ppm [—$\underline{C}$H(NH$_2$)(COONa)] |
| 179.5 ppm (—$\underline{C}$OONa) |

Example 13

A reaction vessel was charged with 180 parts by weight of 3-(2-ethylhexyloxy)propylamine, 180 parts by weight of DL-4,4-dimethyl pyroglutamine acid, and 100 parts by weight of methanol, and the mixture was stirred at 70° C. for 3 hours. The resulting reaction mixture was stripped at 90° C. under reduced pressure to remove the methanol, and 335 parts by weight of white solid was obtained at a yield of 93%. Results of the $^{13}$C-NMR shown in Table 13, below, and absorption at 1685 cm$^{-1}$ (from amide bond) in the measurement of IR spectrum confirmed that the resulting product was an amino acid compound represented by the following formula:

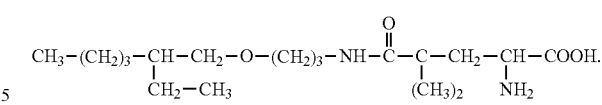

TABLE 13

| $^{13}$C-NMR (CDCl$_3$) |
|---|
| 11.2~74.3 ppm (CH, —$\underline{C}$H$_2$—, —$\underline{C}$H$_3$) |
| 180.9 ppm (—NH—$\underline{C}$O—) |
| 35.0 ppm (—CO—$\underline{C}$) |
| 22.4 ppm (C—$\underline{C}$H$_3$) |
| 41.8 ppm (—C—$\underline{C}$H$_2$—) |
| 56.4 ppm [—$\underline{C}$H(NH$_2$)(COOH)] |
| 179.2 ppm (—$\underline{C}$OOH) |

Example 14

A reaction vessel was charged with 260 parts by weight of 12-amino-1-dodecanol, 184 parts by weight of methyl L-pyroglutamate, and 120 parts by weight of 1,4-dioxane, and the mixture was stirred at 75° C. for 4 hours. The resulting reaction mixture was stripped at 110° C. under reduced pressure to remove the 1,4-dioxane, and 408 parts by weight of white solid was obtained at a yield of 92%. Results of the $^{13}$C-NMR shown in Table 14, below, and absorption at 1685 cm$^{-1}$ (from amide bond) in the measurement of IR spectrum confirmed that the resulting product was an amino acid compound represented by the following formula:

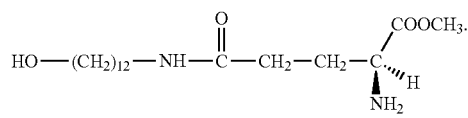

TABLE 14

| $^{13}$C-NMR (CDCl$_3$) |
|---|
| 64.6 ppm (—$\underline{C}$H$_2$—OH) |
| 22~31.9 ppm (—($\underline{C}$H$_2$)$_{10}$—] |
| 39.6 ppm (—$\underline{C}$H$_2$—NH—) |
| 178.4 ppm (—NH—$\underline{C}$O—) |
| 25.2 ppm (—CO—$\underline{C}$H$_2$—CH$_2$—) |
| 28.6 ppm (—CO—CH$_2$—$\underline{C}$H$_2$—) |
| 58.9 ppm [—$\underline{C}$H(NH$_2$)(COOCH$_3$)] |
| 174.8 ppm (—$\underline{C}$OOCH$_3$) |
| 59.3 ppm (—COO$\underline{C}$H$_3$) |

Japanese Patent Application Nos. 2009-281099, 2009-281114 and 2009-281126 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An amino acid-modified organopolysiloxane having an amino acid derivative bonded to at least one silicon atom of the organopolysiloxane segment constituting the backbone of the amino acid-modified organopolysiloxane via an amide bond represented by the following general formula (1):

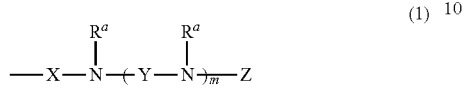
(1)

wherein
X and Y are independently a divalent hydrocarbon group containing 1 to 10 carbon atoms;
m is an integer of 0 to 4;
$R^a$ is a group selected from hydrogen atom, a monovalent hydrocarbon group containing 1 to 4 carbon atoms, and an organic group represented by the following general formula (2):

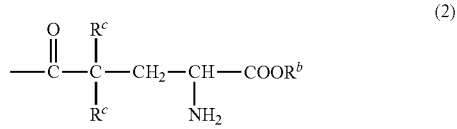
(2)

wherein $R^b$ is hydrogen atom, a monovalent hydrocarbon group containing 1 to 7 carbon atoms, an alkaline metal, or an alkaline earth metal, and $R^c$ is independently hydrogen atom, hydroxy group, or a monovalent hydrocarbon group containing 1 to 10 carbon atoms optionally containing oxygen atom, sulfur atom, or nitrogen atom; and
Z is an organic group represented by the general formula (2).

2. An amino acid-modified organopolysiloxane according to claim 1 which is a compound represented by the average compositional formula (3):

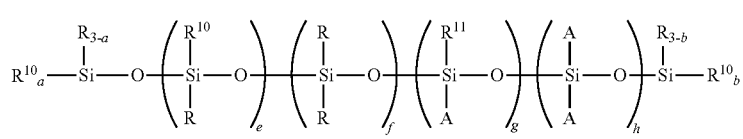
(3)

wherein
R is independently a group selected from hydrogen atom, hydroxy group, an alkyl group containing 1 to 30 carbon atoms, a fluoroalkyl group containing 1 to 30 carbon atoms, an aryl group containing 6 to 30 carbon atoms, and an aralkyl group containing 7 to 30 carbon atoms,
$R^{10}$ is an organic group represented by the general formula (1) of claim 1,
$R^{11}$ is an organic group selected from $R^{10}$ and R, A is an organopolysiloxane segment represented by the following general formula (4):

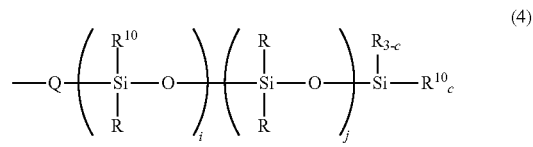
(4)

wherein R and $R^{10}$ are as defined above, and Q is oxygen atom or a divalent hydrocarbon group containing 1 to 3 carbon atoms, and in the formula (3) and general formula (4),
a, b, and c are independently an integer of 0 to 3,
e is an integer of 0 to 500,
f is an integer of 0 to 50,000,
g is an integer of 0 or 1,
h is an integer of 0 or 1,
i is an integer of 0 to 500,
j is an integer of 0 to 10,000,
with the proviso that, $1 \leq a+b+c+e+g+i$ when $R^{11}$ is the same as $R^{10}$ and $1 \leq a+b+c+e+i$ when $R^{11}$ is the same as R.

3. A method for producing the amino acid-modified organopolysiloxane of claim 1 comprising the step of
reacting an amino-modified organopolysiloxane having an amino group bonded to at least one silicon in the organopolysiloxane segment constituting the backbone of the amino-modified organopolysiloxane wherein the amino group is represented by the following general formula (5):

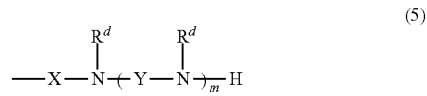
(5)

wherein X, Y, and m are as defined in claim 1, and $R^d$ is hydrogen atom or a monovalent hydrocarbon group containing 1 to 4 carbon atoms with a compound represented by the following general formula (6):

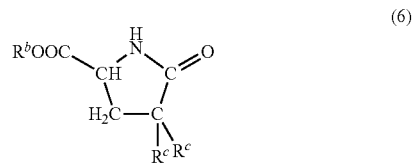
(6)

wherein $R^b$ and $R^c$ are as defined in claim 1.

4. A method for producing an amino acid-modified organopolysiloxane according to claim 3 wherein the amino-modified organopolysiloxane is the one represented by the following average compositional formula (7):

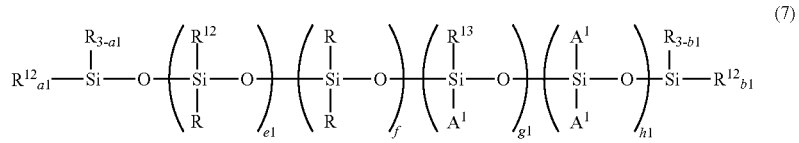

(7)

wherein R is as defined in claim 2, $R^{12}$ is an organic group represented by general formula (5) of claim 3, $R^{13}$ is an organic group selected from $R^{12}$ and R, and $A^1$ is an organopolysiloxane segment represented by the following general formula (8):

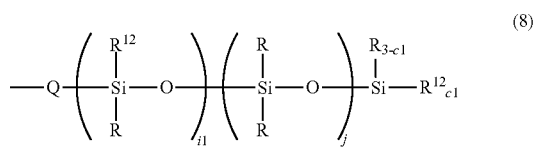

(8)

(wherein R and $R^{12}$ are as defined above), and wherein, in the formula (7) and the general formula (8), a1, b1, and c1 are independently an integer of 0 to 3,
e1 is an integer of 0 to 500,
f is an integer of 0 to 50,000, and
g1 is an integer of 0 of 1,
h1 is an integer of 0 or 1,
i1 is an integer of 0 to 500, and
j is an integer of 0 to 10,000,
with the proviso that $1 \leq a1+b1+c1+e1+g1+i1$ when $R^{13}$ is $R^{12}$ and $1 \leq a1+b1+c1+e1+i1$ when $R^{13}$ is R.

5. A method according to claim 3 wherein the reaction is conducted under temperature conditions of 50 to 160° C.

6. A method according to claim 3 wherein the compound represented by the general formula (6) is pyroglutamine acid.

* * * * *